(12) United States Patent
Addepalli et al.

(10) Patent No.: US 8,188,264 B2
(45) Date of Patent: May 29, 2012

(54) RNAI MEDIATED KNOCKDOWN OF NUMA FOR CANCER THERAPY

(75) Inventors: Murali Addepalli, Maharashtra (IN); Kriti Ray Bimalendu, Maharashtra (IN); Gopavaram Vidyadhar Eswar Chandra Reddy, Maharashtra (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 0 days.

(21) Appl. No.: 12/772,079

(22) Filed: Apr. 30, 2010

(65) Prior Publication Data

US 2010/0286244 A1 Nov. 11, 2010

Related U.S. Application Data

(63) Continuation of application No. 12/132,453, filed on Jun. 3, 2005, now abandoned.

(30) Foreign Application Priority Data

Jun. 15, 2007 (IN) .......................... 1130/MUM/2007

(51) Int. Cl.
*C07H 21/04* (2006.01)
*C07H 21/02* (2006.01)
*A61K 48/00* (2006.01)

(52) U.S. Cl. .......................... 536/24.5; 536/23.1; 514/44

(58) Field of Classification Search ........................ None
See application file for complete search history.

(56) References Cited

U.S. PATENT DOCUMENTS

| 6,287,790 B1 | 9/2001 | Lelievre et al. |
| 6,864,238 B1 | 3/2005 | Tang et al. |
| 2003/0125290 A1 | 7/2003 | Phillips et al. |
| 2005/0255487 A1 | 11/2005 | Khvorova et al. |

FOREIGN PATENT DOCUMENTS

| WO | WO 96/40917 A | 12/1996 | |
| WO | WO 2004/045543 A2 * | 6/2004 | ........................ 514/44 |
| WO | WO 2005/014846 A2 | 2/2005 | |

OTHER PUBLICATIONS

Chang et al., "NuMA is a major acceptor of poly(ADP-ribosyl)ation by tankyrase 1 in mitosis" *Biochem. J.*, vol. 391, pp. 177-184 (2005).

Elbashir et al. "Duplexes of 21-nucleotide RNAs mediate RNA interference in cultured mammalian cells" *Nature* vol. 411, pp. 494-498 (2001).

Goding, "Production of Monoclonal Antibodies: Principles and Practice," 3rd Ed. London: Academic Press, pp. 141-191 and pp. 352-399 (1996).

Henschel, et al., "DEQOR: A web based tool for the design and quality control of siRNAs," *Nucleic Acids Res.*, vol. 32, Web Service Issue, pp. W113-W120 (2004).

Hornung et al., "Sequence-specific Potent Induction of IFN-α by short interfering RNA in plasmacytoid dendritic cells through TLR7," *Nature Medicine* 2005, vol. 11, pp. 263-270 (2005).

Judge, A. D., et al., "Sequence dependent stimulation of the mammalian innate immune response by synthetic siRNA," *Nat. Biotechnol.* 2005; vol. 23, No. 4, pp. 457-462 (2005).

Livak et al., "Analysis of relative gene expression data using real-time quantitative PCR and $2^{-\Delta\Delta Ct}$ method" *Methods* 25, pp. 402-408 (2001).

Miller et al., "Death-Induced Changes to the Nuclear Matrix: The Use of Anti-Nuclear Matrix Antibodies to Study Agents of Apoptosis," Biotechniques, vol. 15, No. 6, pp. 1042-1047, (1993).

Miller et al., "Detection of Nuclear Matrix Proteins in Serum from Cancer Patients," Cancer Res., 52, pp. 422-427 (1992).

Stampfer et al., Evaluation of NMP22 in the Detection of Transitional Cell Carcinoma of the Bladder, Journ. of Urology, vol. 159, pp. 394-398 (1998).

Sui, et al., "A DNA vector based RNAi technology to suppress gene expression in mammalian cells," *Proc. Natl. Acad. Sci.*, vol. 99, No. 8, pp. 5515-5520 (2002).

Ui-Tei, et al., "Guidelines for the selection of highly effective siRNA sequences for mammalian and chick RNA interference," *Nucleic Acid Res.*, vol. 32, No. 3, pp. 936-948 (2004).

Tang et al., "Nuclear mitotic apparatus protein (NuMA): spindle association, nuclear targeting and differential subcellular localization of various NuMA isoforms," Journ. of Cell Science 107, pp. 1389-1402 (1994).

Yang et al. "An unusually long coiled-coil related protein in the mammalian nucleus." *J Cell Biol.*, vol. 116, No. 6, pp. 1303-1317 (1992).

Compton et al., "NuMA is Required for the Proper Completion of Mitosis," *The Journ. of Cell Biol.*, vol. 120, No. 4, pp. 947-957 (1993).

Chinese Office Action cited in related Chinese Patent Application No. 200880103252.x, dated Sep. 7, 2011.

* cited by examiner

*Primary Examiner* — Amy Bowman

(74) *Attorney, Agent, or Firm* — Foley & Lardner LLP

(57) ABSTRACT

This invention relates to the use of short interfering nucleic acid molecules (siRNA) to inhibit Nuclear Mitotic Apparatus Protein (NuMA) gene expression and their use in treatment of disease, including cancer.

5 Claims, 8 Drawing Sheets

SEQUENCE LISTING

<160> NUMBER OF SEQ ID NOS: 12

<210> SEQ ID NO 1
<211> LENGTH: 19
<212> TYPE: DNA
<213> ORGANISM: Homo sapiens

<400> SEQUENCE: 1

```
gaggtacgat tccggagaa                                        19

<210> SEQ ID NO 2
<211> LENGTH: 21
<212> TYPE: DNA
<213> ORGANISM: Homo sapiens

<400> SEQUENCE: 2
gaccatgagg acgggctaaa c                                     21

<210> SEQ ID NO 3
<211> LENGTH: 25
<212> TYPE: DNA
<213> ORGANISM: Homo sapiens

<400> SEQUENCE: 3
cgagaaggat gcacagatag ccatg                                 25

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
gagguacgau uccggagaat t                                     21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
uucuccggaa ucguaccuct t                                     21

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
gaccaugagg acgggcuaaa ctt                                   23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

```
<223> OTHER INFORMATION: Description of Artificial Sequence: Synthetic
      oligonucleotide

<400> SEQUENCE: 7
guuuagcccg uccucauggu ctt                                                  23

<210> SEQ ID NO 8
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cgagaaggau gcacagauag ccatg                                                25

<210> SEQ ID NO 9
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cauggcuauc ugugcauccu ucucggu                                              27

<210> SEQ ID NO 10
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gaggaggaag cgcccaauau ctt                                                  23

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
gauauugggc gcuuccuccu ctt                                                  23

<210> SEQ ID NO 12
<211> LENGTH: 7182
<212> TYPE: DNA
<213> ORGANISM: Homo sapiens

<400> SEQUENCE: 12
gcgctggcgc gagcccacga agaggtacga ttccggagaa tcgcgaggca gagcgggagc          60
gcgcagccag gtggaaacta attctaagcc agactgctgg agatcaccct gttctagtgt         120
```

-continued

| | |
|---|---|
| gtggaggctt ccaccaggag gcgcattgga gtgactgtct ggcatcacca agatgacact | 180 |
| ccacgccacc cggggggctg cactcctctc ttgggtgaac agtctacacg tggctgaccc | 240 |
| tgtggaggct gtgctgcagc tccaggactg cagcatcttc atcaagatca ttgacagaat | 300 |
| ccatggcact gaagagggac agcaaatctt gaagcagccg tgtcagagag actggactt | 360 |
| tgtgtgcagt tttctgcaga aaatcgaaa acatccctct tccccagaat gcctggtatc | 420 |
| tgcacagaag gtgctagagg gatcagagct ggaactggcg aagatgacca tgctgctctt | 480 |
| ataccactct accatgagct ccaaaagtcc cagggactgg gaacagtttg aatataaaat | 540 |
| tcaggctgag ttggctgtca ttcttaaatt tgtgctggac catgaggacg ggctaaacct | 600 |
| taatgaggac ctagagaact tcctacagaa agctcctgtg ccttctacct gttctagcac | 660 |
| attccctgaa gagctctccc cacctagcca ccaggccaag agggagattc gcttcctaga | 720 |
| gctacagaag gttgcctcct cttccagtgg gaacaacttt ctctcaggtt ctccagcttc | 780 |
| tcccatgggt gatatcctgc agaccccaca gttccagatg agacggctga agaagcagct | 840 |
| tgctgatgag agaagtaata gggatgagct ggagctggag ctagctgaga accgcaagct | 900 |
| cctcaccgag aaggatgcac agatagccat gatgcagcag cgcattgacc gcctagccct | 960 |
| gctgaatgag aagcaggcgg ccagcccact ggagcccaag gagcttgagg agctgcgtga | 1020 |
| caagaatgag agccttacca tgcggctgca tgaaacctg aagcagtgcc aggacctgaa | 1080 |
| gacagagaag agccagatgg atcgcaaaat caaccagctt tcggaggaga atggagacct | 1140 |
| ttcctttaag ctgcgggagt ttgccagtca tctgcagcag ctacaggatg ccctcaatga | 1200 |
| gctgacggag gagcacagca aggccactca ggagtggcta gagaagcagg cccagctgga | 1260 |
| gaaggagctc agcgcagccc tgcaggacaa gaaatgcctt gaagagaaga cgaaatcct | 1320 |
| tcagggaaaa ctttcacagc tggaagaaca cttgtcccag ctgcaggata cccacccca | 1380 |
| ggagaagggc gaggtgctgg gtgatgtctt gcagctggaa accttgaagc aagaggcagc | 1440 |
| cactcttgct gcaaacaaca cacagctcca agccagggta gagatgctgg agactgagcg | 1500 |
| aggccagcag gaagccaagc tgcttgctga gcggggccac ttcgaagaag aaaagcagca | 1560 |
| gctgtctagc ctgatcactg acctgcagag ctccatctcc aacctcagcc aggccaagga | 1620 |
| agagctggag caggcctccc aggctcatgg ggcccggttg actgcccagg tggcctctct | 1680 |
| gacctctgag ctcaccacac tcaatgccac catccagcaa caggatcaag aactggctgg | 1740 |
| cctgaagcag caggccaaag agaagcaggc ccagctagca cagaccctcc aacagcaaga | 1800 |
| acaggcctcc cagggcctcc gccaccaggt ggagcagcta agcagtagcc tgaagcagaa | 1860 |
| ggagcagcag ttgaaggagg tagcggagaa gcaggaggca actaggcagg accatgccca | 1920 |
| gcaactggcc actgctgcag aggagcgaga ggcctcctta agggagcggg atgcggctct | 1980 |
| caagcagctg gaggcactgg agaaggagaa ggctgccaag ctggagattc tgcagcagca | 2040 |
| acttcaggtg gctaatgaag cccgggacag tgcccgagacc tcagtgacac aggcccagcg | 2100 |
| ggagaaggca gagctgagcc ggaaggtgga ggaactccag gcctgtgttg agacagcccg | 2160 |
| ccaggaacag catgaggccc aggcccaggt tgcagagcta gagttgcagc tgcggtctga | 2220 |
| gcagcaaaaa gcaactgaga aagaaagggt ggcccaggag aaggaccagc tccaggagca | 2280 |
| gctccaggcc ctcaaagagt ccttgaaggt caccaagggc agccttgaag aggagaagcg | 2340 |
| cagggctgca gatgccctgg aagagcagca gcgttgtatc tctgagctga aggcagagac | 2400 |
| ccgaagcctg gtggagcagc ataagcggga acgaaaggag ctggaagaag agagggctgg | 2460 |
| gcgcaagggg ctggaggctc gattacagca gcttggggag gcccatcagg ctgagactga | 2520 |

```
agtcctgcgg cgggagctgg cagaggccat ggctgcccag cacacagctg agagtgagtg   2580
tgagcagctc gtcaaagaag tagctgcctg gcgtgagcgg tatgaggata gccagcaaga   2640
ggaggcacag tatggcgcca tgttccagga acagctgatg actttgaagg aggaatgtga   2700
gaaggcccgc caggagctgc aggaggcaaa ggagaaggtg gcaggcatag aatcccacag   2760
cgagctccag ataagccggc agcagaacga actagctgag ctccatgcca acctggccag   2820
agcactccag caggtccaag agaaggaagt cagggcccag aagcttgcag atgacctctc   2880
cactctgcag gaaaagatgg ctgccaccag caaagaggtg gcccgcttgg agaccttggt   2940
gcgcaaggca ggtgagcagc aggaaacagc ctcccgggag ttagtcaagg agcctgcgag   3000
ggcaggagac agacagcccg agtggctgga agagcaacag ggacgccagt tctgcagcac   3060
acaggcagcg ctgcaggcta tggagcggga ggcagagcag atgggcaatg agctggaacg   3120
gctgcgggcc gcgctgatgg agagccaggg gcagcagcag gaggagcgtg ggcagcagga   3180
aagggaggtg gcgcggctga cccaggagcg gggccgtgcc caggctgacc ttgccctgga   3240
gaaggcggcc agagcagagc ttgagatgcg gctgcagaac gccctcaacg agcagcgtgt   3300
ggagttcgct accctgcaag aggcactggc tcatgccctg acggaaaagg aaggcaagga   3360
ccaggagttg gccaagcttc gtggtctgga ggcagcccag ataaaagagc tggaggaact   3420
tcggcaaacc gtgaagcaac tgaaggaaca gctggctaag aaagaaaagg agcacgcatc   3480
tggctcagga gcccaatctg aggctgctgg caggacagag ccaacaggcc caagctgga   3540
ggcactgcgg gcagaggtga gcaagctgga acagcaatgc cagaagcagc aggagcaggc   3600
tgacagcctg gaacgcagcc tcgaggctga gcgggcctcc cgggctgagc gggacagtgc   3660
tctggagact ctgcagggcc agttagagga gaaggcccag gagctagggc acagtcagag   3720
tgccttagcc tcggcccaac gggagttggc tgccttccgc accaaggtac aagaccacag   3780
caaggctgaa gatgagtgga aggcccaggt ggcccgggc cggcaagagg ctgagaggaa   3840
aaatagcctc atcagcagct tggaggagga ggtgtccatc ctgaatcgcc aggtcctgga   3900
gaaggagggg gagagcaagg agttgaagcg gctggtgatg gccgagtcag agaagagcca   3960
gaagctggag gagaggctgc gcctgctgca ggcagagaca gccagcaaca gtgccagagc   4020
tgcagaacgc agctctgctc tgcgggagga ggtgcagagc ctccgggagg aggctgagaa   4080
acagcgggtg gcttcagaga acctgcggca ggagctgacc tcacaggctg agcgtgcgga   4140
ggagctgggc caagaattga aggcgtggca ggagaagttc ttccagaaag agcaggccct   4200
ctccaccctg cagctcgagc acaccagcac acaggccctg gtgagtgagc tgctgccagc   4260
taagcacctc tgccagcagc tgcaggccga gcaggccgct gccgagaaac gccaccgtga   4320
ggagctggag cagagcaagc aggccgctgg gggactgcgg gcagagctgc tgcgggccca   4380
gcgggagctt ggggagctga ttcctctgcg gcagaaggtg gcagagcagg agcgaacagc   4440
tcagcagctg cgggcagaga aggccagcta tgcagagcag ctgagcatgc tgaagaaggc   4500
gcatggcctg ctggcagagg agaaccgggg gctgggtgag cgggccaacc ttggccggca   4560
gtttctggaa gtggagttgg accagccccg ggagaagtat gtccaagagt ggcagccgt   4620
acgtgctgat gctgagaccc gtctggctga ggtgcagcga aagcacagag cactgcccg   4680
ggagctggag gtgatgactg ccaagtatga gggtgccaag gtcaaggtcc tggaggagag   4740
gcagcggttc caggaagaga ggcagaaact cactgcccag gtggagcagc tagaggtatt   4800
tcagagagag caaactaagc aggtggaaga actgagtaag aaaactggctg actctgacca   4860
agccagcaag gtgcagcagc agaagctgaa ggctgtccag gctcagggag gcgagagcca   4920
```

```
gcaggaggcc cagcgcctcc aggcccagct gaatgaactg caagcccagt tgagccagaa    4980
ggagcaggca gctgagcact ataagctgca gatggagaaa gccaaaacac attatgatgc    5040
caagaagcag cagaaccaag agctgcagga gcagctgcgg agcctggagc agctgcagaa    5100
ggaaaacaaa gagctgcgag ctgaagctga acggctgggc catgagctac agcaggctgg    5160
gctgaagacc aaggaggctg aacagacctg ccgccacctt actgcccagg tgcgcagcct    5220
ggaggcacag gttgcccatg cagaccagca gcttcgagac ctgggcaaat tccaggtggc    5280
aactgatgct ttaaagagcc gtgagcccca ggctaagccc cagctggact tgagtattga    5340
cagcctggat ctgagctgcg aggaggggac cccactcagt atcaccagca agctgcctcg    5400
tacccagcca gacggcacca gcgtccctgg agaaccagcc tcacctatct cccagcgcct    5460 gcccccaag gtagaatccc tggagagtct ctacttcact cccatccctg ctcggagtca    5520
ggcccccctg gagagcagcc tggactccct gggagacgtc ttcctggact cgggtcgtaa    5580
gacccgctcc gctcgtcggc gcaccacgca gatcatcaac atcaccatga ccaagaagct    5640
agatgtggaa gagccagaca cgccaactc atcgttctac agcacgcggt ctgctcctgc    5700
ttcccaggct agcctgcgag ccacctcctc tactcagtct ctagctcgcc tgggttctcc    5760
cgattatggc aactcagccc tgctcagctt gcctggctac cgccccacca ctcgcagttc    5820
tgctcgtcgt tcccaggccg gggtgtccag tggggcccct ccaggaagga acagcttcta    5880
catgggcact tgccaggatg agcctgagca gctggatgac tggaaccgca ttgcagagct    5940
gcagcagcgc aatcgagtgt gccccccaca tctgaagacc tgctatcccc tggagtccag    6000
gccttccctg agcctgggca ccatcacaga tgaggagatg aaaactggag acccccaaga    6060
gaccctgcgc cgagccagca tgcagccaat ccagatagcc gagggcactg gcatcaccac    6120
ccggcagcag cgcaaacggg tctccctaga gccccaccag ggccctggaa ctcctgagtc    6180
taagaaggcc accagctgtt tcccacgccc catgactccc cgagaccgac atgaagggcg    6240
caaacagagc actactgagg cccagaagaa agcagctcca gcttctacta aacaggctga    6300
ccggcgccag tcgatggcct tcagcatcct caacacaccc aagaagctag gaacagcct    6360 tctgcggcgg ggagcctcaa agaaggccct gtccaaggct tccccaaca ctcgcagtgg    6420 aacccgccgt tctccgcgca ttgccaccac cacagccagc gccgccactg ctgccgccat    6480
tggtgccacc cctcgagcca agggcaaggc aaagcactaa agggccagta ccagtgagtg    6540
gccccacctg tgtccccgat gctgacctca cctggtcctc cgcctactgt ccctctcagt    6600
gccttctctc agctcccagg ccaacagtag ccaaacccct agagacagtg atgcctgccc    6660
gcaccctggc ctggtccctg gtccttcact ggcgccttct cggagctggc caggggggcc    6720
tggagcatgg acagtgtggg cgctctccct accttgcctc cttttttctt aaagcaaagt    6780
cacttctcca tcacaaccag atttgaggct ggttttgatg gctgggtcct tgggcctggc    6840
cagtcttcct cttagcctct ggatctagaa gggaccataa gaggagtagg ccctggttcc    6900
tgctgtcctg gtggctgggc ccagcagggg ccctcactct tgaagtccag gactgggtct    6960
gacctggtgg gagcacctgc cagaggatgc tctttcccag gacggatggg ccctatgtct    7020
caggagtggg gttgggggac agccttcagc agcagctcac accctacctt cccagacttt    7080
gcactggggt gggatttgga gtgatgggaa ggttttttaag ggccggggat ggatcttttc    7140
taaatgttat tacttgtaaa taaagtctat ttttctcccg tg                       7182
```

RNAI MEDIATED KNOCKDOWN OF NUMA FOR CANCER THERAPY

CROSS-REFERENCE TO RELATED PATENT APPLICATIONS

The present application is a continuation of U.S. patent application Ser. No. 12/132,453, filed Jun. 3, 2008, which claims the benefit of the filing date of Indian Provisional Patent Application No. 1130/MUM/2007 filed Jun. 15, 2007. The contents of these applications are incorporated herein by reference in their entirety.

FIELD OF THE INVENTION

The present invention relates to the field of short interfering ribonucleic acid (siRNA) molecules capable of down-regulating NuMA gene expression, and their use in cancer therapy.

BACKGROUND OF THE INVENTION

Nuclear mitotic apparatus protein (NuMA) is a large 236 KDa coiled-coil protein with a globular head and tail, and is a predominantly nuclear protein that is present in the interphase nucleus and is concentrated in the spindle pole of mitotic cells. NuMA is also known as centrophilin, SPN, SP-H, 1H1/1F1, and W1 (Tang et al. "Nuclear mitotic apparatus protein (NuMA): spindle association, nuclear targeting and differential subcellular localization of various NuMA isoforms." *Journal of Cell Science* 107: 1389-1402 (1994)). NuMA converges on microtubules at the minus ends, a function that is essential for spindle organization. In dividing cells, upon phosphorylation, NuMA disperses into the cytoplasm, associates with cytoplasmic dynein/dynactin to form a complex, and translocates along microtubules to the spindle poles where it organizes and tethers microtubules to spindle poles. NuMA becomes dephosphorylated, loses its association with dynein/dynactin, and releases from spindle poles after anaphase onset to allow spindle disassembly and reformation of interphase daughter nuclei. The cell-cycle-dependent phosphorylation of NuMA is regulated by the balanced activities of protein kinases and phosphatases. It has been shown that phosphorylation of NuMA by cyclin B/cdc2 kinase allows NuMA to release from the nucleus and to associate with centrosomes and/or microtubules at the spindle poles, while NuMA's dephosphorylation due to the cyclin B degradation allows NuMA to dissociate from the spindle poles after anaphase onset. Overexpression of NuMA interferes with spindle-associated dynein localization and promotes multipolar spindle formation and cancer. On the other hand, NuMA is absent in many kinds of non-proliferating cells and highly differentiated cells. NuMA also functions during meiotic spindle organization in male and female germ cells. Degradation of NuMA results in the breakdown of normal nuclear structure, and has been used as a marker of cell apoptosis.

Any discrepancy in the function of NuMA leads to disruption of microtubule focusing at spindle poles leading to splaying of microtubule ends. NuMA resides in the nucleus during interphase and becomes transiently associated with mitotic centrosomes after multiple steps of phosphorylations. NuMA responds to external signals such as hormones that induce cell divisions or heat shock that induce apoptosis. At prophase NuMA disperses in the cytoplasm and associates with microtubules. During meta- or anaphase NuMA gets associated with chromatin and finally to the reconstituted nucleus. NuMA is a cell cycle-related protein essential for normal mitosis that gets degraded in early apoptosis. NuMA forms a complex with cytoplasmic dynein and dynactin. The depletion of the complex lead to failure in normal assembly of mitotic spindles. NuMA gets PARsylated by tankyrase-1 during mitosis.

Studies conducted by Comptom and Cleveland (1993) have suggested that NuMA is required for the proper terminal phases of chromosome separation and/or nuclear reassembly during mitosis. Microinjection of anti-NuMA antibodies into early mitotic or metaphase cells was found by Yang et al. "An unusually long coiled-coil related protein in the mammalian nucleus." *J. Cell Biol.* 116(6): 1303-1317 (1992), to prevent the formation or cause the collapse of the mitotic spindle apparatus, thus suggesting that NuMA may play an important role during mitosis.

Several studies have described a link between NuMA and cancer, but have not established that NuMA inhibition can treat cancer. NuMA is released from cells undergoing apoptosis (Miller et al., Biotechniques, 15:1042, 1993) and has been detected in the serum of patients with a wide range of cancers (Miller et al., Cancer Res., 52:422, 1992), and specifically in the urine of patients with bladder cancer (Stampfer et al., J. Urol., 159:394, 1998).

In WO/2005/014846, NuMA is regarded as a relevant target in methods for identifying risk of breast cancer in a subject and/or a subject at risk of breast cancer, reagents and kits for carrying out the methods, methods for identifying candidate therapeutics for treating breast cancer, and therapeutic methods for treating breast cancer in a subject. Variations in the NuMA gene were associated with familial breast cancer risk.

U.S. Pat. No. 6,287,790 describes a method for distinguishing malignant and proliferating non-malignant cells by cell immunostaining using a NuMA specific antibody, and microscopic analysis of NuMA distribution within each nucleus.

U.S. Pat. No. 6,864,238 describes polypeptides, and polynucleotides encoding such polypeptides, that are useful for destabilizing microtubules. Since microtubules play an essential role in cell division, which occurs more frequently in tumor cells, the polypeptides and polynucleotides can be useful in preparing a composition for inhibiting cell proliferation for treating a tumor.

US 20030125290 describes a composition comprising useful triethyleneglycol cholesteryl oligonucleotides for induction of response in a cell, including but not limited to inhibition of cellular proliferation, induction of cell cycle arrest, induction of caspase activation, cleavage of poly(ADP-ribose) polymerase, induction of apoptosis or modulation of extracellular matrix-cell interactions, or combinations thereof, in cancer cells or synovial cells, and methods of using this composition for treating disease. The release of NuMA was used as a measure of apoptosis.

WO9640917A describes methods and compositions for identifying proteins which interact non-covalently with NuMA in a cell, novel proteins identified by the method, and methods and compositions for interfering with this interaction in vivo.

El Bashir et al. "Duplexes of 21-nucleotide RNAs mediate RNA interference in cultured mammalian cells" *Nature* 411: 494-498 (2001), describes a 21 nucleotide siRNAs against NuMA downregulating NuMA protein expression in vitro.

Chang et al., "NuMA is a major acceptor of poly(ADP-ribosyl)ation by tankyrase 1 in mitosis" *Biochem. J.*: 391:

117-184 (2005), describe the use of siRNA against NuMA to study NuMA function in human cells in vitro.

SUMMARY OF THE INVENTION

The present invention is directed to siRNA which targets the NuMA mRNA. In one embodiment, the invention comprises siRNAs that target NuMA at nucleotides 20-40, 578-598, or 905-929 of Genbank Accession Number NM_006185. In related embodiments, the siRNA includes those directed against SNPs of the NuMA molecule. In related embodiments, the siRNA targets a sequence selected from the group consisting of SEQ ID NO:1; SEQ ID NO:2; and SEQ ID NO:3.

In one embodiment, at least one strand of the siRNA of the invention is between 19 and 30 nucleotides in length. In related embodiments, siRNA has a structure selected from the group consisting of:
SEQ ID NO: 4 and SEQ ID NO: 5;
SEQ ID NO: 6 and SEQ ID NO: 7;
SEQ ID NO: 8 and SEQ ID NO: 9; and
SEQ ID NO: 10 and SEQ ID NO: 11.

The invention is also directed to a method of reducing NuMA expression in a target cell by administration of siRNA, including the siRNA of the invention.

The invention also includes a method of treating cancer by administration of siRNA against NuMA. In one embodiment, the siRNA targets at nucleotides 20-40, 578-598, or 905-929 of Genbank Accession Number NM_006185. In another, the siRNA targets the equivalent SNPs thereof. In related embodiments, the siRNA targets a sequence selected from the group consisting of SEQ ID NO:1; SEQ ID NO:2; and SEQ ID NO:3.

In further embodiments, the method of treating cancer uses a siRNA in which at least one nucleotide strand is between 19 and 30 nucleotides. In related embodiments, the siRNA has a structure selected from the group consisting of:
SEQ ID NO: 4 and SEQ ID NO: 5;
SEQ ID NO: 6 and SEQ ID NO: 7;
SEQ ID NO: 8 and SEQ ID NO: 9; and
SEQ ID NO: 10 and SEQ ID NO: 11.

The method of treating cancer may be practiced on any cancer. In one embodiment, the cancer is selected from the group consisting of cervical cancer, epidermoid cancer, oral cancer, glioma, leukemia, brain cancer, esophageal cancer, stomach cancer, bladder cancer, pancreatic cancer, cervical cancer, head and neck cancer, ovarian cancer, melanoma, lymphoma, and multidrug resistant cancer. In another embodiment, the cancer is selected from the group consisting of colorectal cancer, breast cancer, lung cancer, and prostrate cancer.

The invention also includes pharmaceutical compositions suitable for the treatment of cancer, comprising a siRNA of the invention and a pharmaceutically acceptable excipient.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the description of specific embodiments presented herein.

FIG. 1A: CCL-247 cells transfected with RINA 10 show localization of NuMA at spindle poles as well as specific staining in cytoplasm. Arrowhead indicates the spindle pole localized NuMA.

FIG. 1B: CCL-247 cells transfected with RINA 25 show absence of localization of NuMA at the spindle poles as well as specific staining in the cytoplasm. Arrowhead indicates absence of spindle pole localized NuMA as well as absence of NuMA-specific staining in the cytoplasm.

FIG. 4: Cell cycle analysis of the colorectal cancer cell line, CCL-247 after 72 h of transfection with RINA 25, RINA 10, or untreated. M1 represents the number of cells that were $G_o/G_1$ phase of the cell cycle, M2 represents the number of cells in S phase of cell cycle, M3 represents the number of cells that were in $G_2$ phase of cell cycle and M4 represents cells undergoing apoptosis.

DETAILED DESCRIPTION

Definitions

Figure 1:
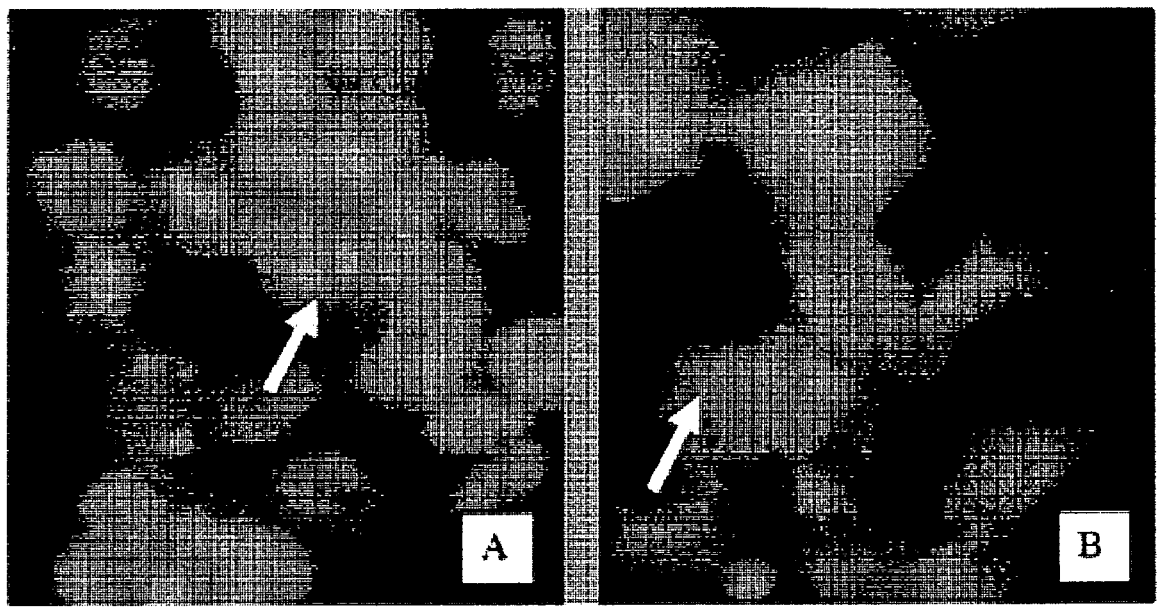
FIG. 1: Colorectal cancer cells CCL-247 were transfected with RINA 25 and RINA 10 and assayed for localization of NuMA at spindle poles by immunofluorescence assay. Scale 200×.

The terms "short interfering nucleic acid," "siNA" or "SINA" molecules, "short interfering RNA," "siRNA," "short interfering nucleic acid molecule," "short interfering oligonucleotide molecule," as used herein, refer to any nucleic acid molecule capable of inhibiting or down-regulating gene expression by an RNA interference mechanism.

The term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA or analogs of naturally occurring RNA.

The term "modulate" as used herein means that the expression of the gene or level of RNA molecule or equivalent RNA molecules encoding one or more protein or protein subunits, or activity of one or more protein subunits, is up-regulated or down-regulated such that the expression, level or activity is greater than or less than that observed in the absence of the modulator. The term "modulate" encompasses "inhibit" but the use of the terms is not limited in this definition.

The term "gene" as used herein means a nucleic acid that encodes a RNA sequence including but not limited to structural genes encoding a polypeptide.

The term "Nuclear associated mitotic protein" or "NuMA" as used herein refers to any NuMA protein, peptide, or polypeptide having NuMA or Centrophilin activity such as encoded by genbank accession number NM_006185. It also refers to nucleic acid sequences encoding NuMA protein, peptide, or polypeptide having isoforms, mutant genes, splice variants and polymorphisms.

The term "target nucleic acid" as used herein means any nucleic acid sequence whose expression or activity is to be modulated. The target nucleic acid can be DNA or RNA.

The term "sense region" as used herein means a nucleotide sequence of a siNA molecule having the same sequence as a target nucleic acid sequence. In addition, the sense region of a siRNA molecule can comprise a nucleic acid sequence having complementarity to a antisense region of the siNA molecule.

The term "antisense region" as used herein means a nucleotide sequence of a siRNA molecule having complementarity to a target nucleic acid sequence. The term can also encompass a nucleic acid sequence having complementarity to a sense region of the siRNA molecule.

The term "complementarity" as used herein means that the nucleic acid can form hydrogen bonds with another nucleic acid molecule (e.g. A-T, A-U, G-C).

The term "cancer" or "proliferative diseases" as used herein means any disease, condition, trait, genotype or phenotype characterized by unregulated cell growth or replication as is known in the art. It can include all types of cancer, tumors, lymphomas, carcinomas that can respond to the modulation of disease related NuMA gene expression in a cell or tissue alone or in combination with other therapies.

Unless otherwise specified, "a" or "an" means "one or more."

The present invention is directed to modulation of NuMA gene expression through a short interfering nucleic acids (siRNA) molecule. In particular the present invention relates to compounds, compositions and uses of 19-30 mer, including 21, 23 or 27 mer short interfering nucleic acid (siRNA) molecules directed against NuMA in modulation of its expression. The compounds of the present invention are useful in therapy of cancer either alone or in combination with other treatments or therapies.

In one embodiment, the invention provides modulation of NuMA gene expression through a short interfering nucleic acids (siRNA) molecule, including 19-30, including especially 21, 23 and 27-mers directed against NuMA. In further embodiments, the invention provides SNP-specific siRNA molecules so as to offer personalized treatment to patients. Cancer associated SNPs are known. See, e.g. WO 2005/014846A2, especially pages 145-150. Examplary SNPs include the following, with breast-cancer associated SNPs underlined: A-2315 bp(T/A), G-2337 bp(A/G), C-2381 bp(G/C), G-2617 bp(A/G), G-2932 bp(T/C), G-3369 bp(A/G), G-4422 bp(G/A), G-5896 bp(C/T), C-5981(C/A), G-5473 bp(T/C), G-5516 bp(G/T), C-6034 bp(C/T), C-6048 bp(C/A), G-6145(C/T), C-6288 bp(G/A), T-5288 bp(C/T).

In related embodiments, such 19-30 mer, including 21, 23 or 27 mer siRNA molecules are useful for the treatment of different types of cancers, including breast, lung, prostate, colorectal, cervical, epidermoid and oral cancers. In further embodiments, the siRNA molecules of the invention can be used alone or in combination with other therapies for effective management of cancer treatment.

The invention also includes compositions of 19-30 mer, including 21, 23 and 27 mer siRNA, which can be combined with conjugates not limiting to lipids, polymers and monoclonal antibodies.

While some embodiments of the invention focus on siRNA, the disclosure is not to be construed as limited to siRNA, but also encompasses related compositions and methods practiced with short nucleic acid molecules double stranded RNA (dsRNA), micro RNA (mRNA), deoxyribose nucleic acid intereference (DNAi) and short hairpin RNA (shRNA), enzymatic nucleic acid molecules or antisense nucleic acid molecules.

The short nucleic acid molecules can be unmodified or modified chemically. In certain embodiments the present invention relates to 19-30 mer, including 21, 23 or 27-mer siRNA. The efficiency of siRNA may be determined by the ability to reduce the quantity of the target protein so that the functional properties associated with that protein gets impaired.

In another embodiment 19-30 mer, including 21, 23 or 27 mer siRNA molecules can be synthesized either chemically or enzymatically or expressed from a vector. In certain embodiments, there is provided chemically synthesized siRNA which can be used to reduce expression levels of NuMA either alone or in combination with other siRNA directed against genes that are responsible for regulating various cancers.

In certain embodiments, the present invention provides siRNA molecules for treatment of various types of cancers which include breast, lung, prostate, colorectal, cervical, epidermoid, oral cancers, glioma and leukemia.

In one embodiment, the present invention provides techniques used to validate the efficacy of 19-30 mer, including 21, 23 or 27 mer siRNA molecules with biomarkers of cancer.

The present invention provides the efficacy testing with specific biomarkers of cancer such as PCNA, Ki-67, and BCL-2 antigen expression.

In one embodiment, the present invention provides a combination of siRNAs targeting NuMA for the treatment of various types of cancers which include breast, lung, prostate, colorectal, cervical, epidermoid, oral cancers, glioma and leukemia.

In yet another embodiment, the present invention provides an siRNA molecule which can be used alone or in combination with other siRNA or small molecules able to inhibit NuMA expression and such proteins which are associated with cancer or any other conditions or disease that respond to the levels of NuMA in a cell or tissue. One embodiment is the use of siRNA of the present invention in any therapy of genes encoding a sequence of NuMA shown in table I, corresponding to Genbank Accession Number NM_006185.

Although the present invention is related to regulate NuMA expression, the embodiments includes all homologs, single nucleotide polymorphs (SNPs), and transcript variants of NuMA and other genes involved in the NuMA regulatory pathway.

In one embodiment the nucleic acid molecule of the present invention comprises 19, 20, 21, 22, 23, 24, 25, 26, 27, 28, 29 or 30 base pairs on at least one strand.

In another embodiments the nucleic acid molecule of the present invention comprises 19, 20, 21, 22, 23, 24, 25, 26, 27, 28, 29 & 30 base pairs complementary to RNA having a NuMA nucleic acid sequence.

In one embodiment, a siRNA molecule of the present invention comprises a double stranded RNA, wherein one strand of the RNA is complimentary to the RNA of NuMA. In another embodiment, a siRNA molecule of the present invention comprises a double stranded RNA, wherein one strand of the RNA comprises a portion of a sequence of RNA having a NuMA sequence.

In another embodiment, an expression vector encodes for the expression of a nucleic acid molecule of the invention.

In one embodiment, the invention provides a mammalian cell, for example a human cell, including a nucleic acid molecule of the invention.

The present invention provides a method of down-regulating NuMA activity in a cell, comprising contacting the cell with a nucleic acid molecule of the invention under conditions suitable for down-regulating NuMA activity.

The present invention also provides a method of treatment of a subject having a condition associated with an elevated level of NuMA, comprising contacting cells of the subject with a nucleic acid molecule of the present invention under conditions suitable for such treatment.

In one embodiment, the present invention also provides a method of treatment of a subject having a condition associated with the level of NuMA, comprising contacting cells of the subject with the nucleic acid molecule of the present invention, under conditions suitable for treatment.

In one embodiment, a method of treatment of the invention further comprises the use of one or more drug therapies under conditions suitable for said treatment. Dug therapies contemplated by the invention include monoclonal antibodies, chemotherapy, or radiation therapy, or a combination thereof.

The present invention also provides a method of treatment for cancer, including but not limited to breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer, the method comprising administering to a subject the nucleic acid molecule of the invention under conditions suitable for said treatment.

The present invention provides compositions comprising the nucleic acid molecules of the invention in a pharmaceutically acceptable carrier.

The invention also provides a method of administering to a cell, such as mammalian cell (e.g. human cell), where the cell can be in culture or in a mammal, such as a human, a nucleic acid molecule of the instant invention, the method comprising contacting the cell with the nucleic acid molecule under conditions suitable for such administration. The method of administration can be in the presence of a delivery reagent, for example a lipid, cationic lipid, phospholipids or liposome.

The present invention provides compounds of siRNA their use in modulation of NuMA gene expression. The compounds were designed and studied as follows:
1. Design of siRNA
2. Preparation of siRNA
3. Efficacy testing of the compounds
4. Comparative data of 21, 23, and 27 mer siRNA molecules
5. Potency evaluation in animal models The design of siRNA involved the design of 21, 23, and 27 nucleotide molecules for modulation of NuMA. For all siRNA, irrespective of their length, the following general requirements were considered:

i. No runs of 4 or more consecutive A, T, G, or U nucleotides were allowed ii. The following sequences were avoided because they are responsible for inducing an interferon response: (A) 5'-UGUGU-3' and (B) 5'-GUCCUUCAA-3'.

iii. Each siRNA duplex was checked in-silico to avoid silencing of off-target effects, using a BLAST search under the following parameters:

A. Low complexity filtering was removed to avoid insignificance by BLAST resulting in limited or no query sequencer.

B. The word size was set to 7 letters, the minimum value for the algorithm.

C. The expect value threshold was set at 1000 to avoid the probability of short sequence occurrence. Further, the target gene NuMA was screened for accessible sites and the siRNA was synthesized considering the ORF sequences.

The synthesis of siRNA was done by commercially available methods. Most commonly these could be synthesized by standard chemical techniques provided by Qiagen. The chemical methods involve the addition of chemically protected monomeric units called phosphamidites sequentially to generate the desired oligonucleotide sequence. The synthesis involves mainly four steps such as coupling, capping, oxidation and 5'-deprotection. The purification of the siRNA molecules was done either by PAGE, desalting or by IE-HPLC. The quality of each siRNA was analyzed by MALDI-TOF and the yields were determined by integrated spectrophotometer.

Efficacy testing of the siRNA molecules was done in different cell lines. The following cell lines were obtained from the ATCC and were cultured as per the recommendation of the ATCC: MCF-7 (breast cancer), SKBR-3(breast cancer), PC3 (prostate cancer), A549 (lung cancer), A431 (skin cancer), and HeLa (cervical cancer). Cell lines were transfected with siRNAs and incubated.

The transfection efficiencies were obtained for each cell line by counting the number of cells showing Cy3 labeled siRNA after 16 hours of transfection.

Apart from the percent transfection, the morphological features of the cell lines were also observed in comparison with the untreated cell lines.

The potencies of the different length siRNAs were checked by their efficiency in inhibiting proliferation of cancer cell lines. After transfection of siRNA for 72 hours, the cells were incubated with 5-bromo-2-deoxyuridine (BrdU) as per the protocol of Calbiochem. This test determines the ability to incorporate BrdU into DNA of actively proliferating cells. The quantity of BrdU incorporated was estimated by the absorbance values and was compared with the mock treated cells. It is a known fact that incorporation of BrdU occurs only when there is DNA synthesis. During the S-phase of mitosis synthesis of DNA occurs resulting in doubling of chromosomes. In cancer cells, the number of cells that undergo the process of DNA synthesis indicates the growing potential of cells resulting in growth of tumor. Thus the amount of BrdU incorporated into the cells is directly proportionate to the growing potential of tumor cells.

The cells transfected with the siRNA were also analyzed for specific mRNA knockdown effects using real time quantitative PCR analysis. The relative mRNA quantities of NuMA in cells transfected either with siRNA specific for NuMA or scrambled siRNA, was determined, and the fold change in mRNA levels was determined by the protocol of Kenneth J L and Thomas D S "Analysis of relative gene expression data using real-time quantitative PCR and $2^{-\Delta Ct}$ method" *Methods* 25: 402-408 (2001).

The proliferative and metastasis potential of cancer cell lines treated with the siRNA molecules was obtained by measuring the levels of PCNA (proliferative cell nuclear antigen) or Ki-67 antigen.

The protein levels of NuMA were analyzed by western blot. While transfections of siRNA results in a successful knockdown of the target mRNA levels, the cells have various mechanisms to compensate for the loss of mRNA, such as by enhancing gene expression so as to meet the required protein demand of the cell. Hence the efficacy of siRNA in the present invention is determined by the ability to reduce the quantity of the target protein so that the functional properties associated with that protein is impaired, rather than measuring only the level of mRNA.

As stated earlier, the inhibition in the protein levels of NuMA has various effects on metabolic activity of the cells, which leads to functional impairment of cells. This can be measured by colony forming assays, which basically identifies the ability of the single cancer cell to initiate cell cycle processes resulting in development of tumors if the cells metastasize.

The cytotoxicity of the transfected cell lines with siRNA was studied by analyzing the amount of LDH released into the medium due to compromise on membrane integrity. As described earlier, the knockdown of NuMA results in failure of cells to divide as a result of inability of spindle pole to organize properly. This results in activation of mitotic check points resulting in arrest of cell cycle. These cells may undergo a loss of membrane integrity, resulting in release of cytosolic LDH.

NuMA is found to be localized at the spindle poles and is responsible for focus of minus ends of microtubules at the spindle poles. In order to be functional during cell division, NuMA needs to be localized at appropriate locations and quantities. Absence of co-localization of NuMA with the spindle pole leads to defective spindle assembly. Even though methods such as mRNA quantification and protein quantification are available, these methods do not indicate the minimum threshold levels of NuMA required for normal cell function. Hence the present invention aims to determine the quantity of NuMA that gets co-localized at the site of its action in comparison with the mock treated controls.

The effect of siRNAs on interferon production was evaluated, to determine if there was any undesirable response to the introduction of foreign nucleic acid.

Preclinical evaluation of siRNAs was performed by measuring the ability of siRNAs to inhibit tumor growth, or cause tumor regression. Six to 8 week old Nude mice were injected with colorectal cancer cell line CCL-247 (obtained from ATCC) at a density of 10 million cells in 100 µL of volume, either subcutaneously or intravenously. Once Xenograft tumors reached a size of 80-100 mm$^3$ the tumors were treated with siRNA against NuMA.

The RINA 25 treated animals showed knockdown of NuMA protein and tumor regression was observed in one of the three treated animals.

The following examples are included to demonstrate certain embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLES

Example 1

Design of 21, 23, and 27Mer siRNA for Modulation of NuMA 21, 23 or 27 mers were designed based on the literature of Henshel, A et al., "DEQOR: A web based tool for the design and quality control of siRNAs," *Nucleic Acids Res.* 2004; 32: W113-W120; Ui-Tei, K, et al., "Guidelines for the selection of highly effective siRNA sequences for mammalian and chick RNA interference," *Nucleic Acid Res.* 2004; 32(3): 936-48; Sui, G., et al., "A DNA vector based RNAi technology to suppress gene expression in mammalian cells," *Proc. Natl. Acad. Sci. USA* 2002; 26(2): 199-213; Kim, D. H., et al., "Synthetic dsRNA dicer-substrates enhance RNAi in plasmacytoid dendritic cells through TLR7," *Nature Medicine* 2005; 11: 263-270; Judge, A. D., et al., "Sequence dependent stimulation of the mammalian innate immune response by synthetic siRNA," *Nat. Biotechnol.* 2005; 23(4): 457-62. The following basic requirement were met when designing siRNAs:

For Designing 21mer siRNAs:
  1. All siRNA has GC content between 30-50%
  2. 3'—of each siRNA has an overhang of dTdT
For Designing 23mer siRNAs:
  1. All siRNAs start at 5'-either with G/C
  2. 3'—of each siRNA strand has an overhang of dTdT
  3. The GC content of the duplex is between 40-50%
For Designing 27mer siRNAs:
  1. The GC content of the duplex is between 40-55%.
  2. The sense strand is 25 nucleotides whereas antisense strand is 27 nucleotides, resulting in an overhang at 3'—of the antisense strand.

3. The last 2 nucleotides of the 3'-sense strand contain deoxysugar instead of a ribosugar back bone.
4. 5'—of the sense strands contains an overhang while the 3'—is blunt ended.

The sequence of NuMA was screened for accessible sites which could meet the above mentioned criteria using various algorithms online available, and additional manual analysis. Based on these criteria, the following sites were identified.

molecule reached the desired length it was further de-protected, cleaved from the solid support and analyzed for purity and yield.

Purification:

The siRNAs were purified by desalting or PAGE (Polyacrylamidegel electrophoresis) or by Ion Exchange-High Performance Liquid Chromatography (IE-HPLC). The quality of each nucleotide strand was analyzed by MALDI-TOF

TABLE 1

Target ORF sequences of NuMA for which siRNA were synthesized

| SIRNA | RINA | Gene ID | Target Sequence in ORF | Start site | End site | SEQ ID NO: |
|---|---|---|---|---|---|---|
| 1 (21 mer) | 1 | NM_006185 | 5'-GAGGTACGATTCCGGAGAA-3' | 20 | 40 | 1 |
| 2 (23 mer) | 9 | NM_006185 | 5'-GACCATGAGGACGGGCTAAAC-3' | 578 | 598 | 2 |
| 3 (27 mer) | 25 | NM_006185 | 5'-CGAGAAGGATGCACAGATAGCCATG-3' | 905 | 929 | 3 |

Example 2

Preparation of siRNA Molecules

The RNAi molecules were synthesized by chemical means employing commercially available machinery from various companies such as Applied Biosystems, Beckman, etc. These could be synthesized by any of the following standard chemical methods or procured from Qiagen. The chemical methods were classified based on the type of protecting group incorporated at the 2'-carbon position of the ribose sugar— and yields were determined by integrated spectrophotometer absorbance at 30 nm. During quality control by MALDI-TOF, a difference of 4 atomic mass units was the maximum allowed difference from that predicted. After obtaining comparable yields for each strand, the sense and antisense strands were annealed and vacuum lyophilized. At the time of use, the lyophilized powders were suspended in RNA suspension buffer (100 mM KCl, 30 mM HEPES buffer (pH 7.5), and 1 mM $MgCl_2$), heated for 1 min at 90° C., incubated at 37° C. for 1 h to dissolve the lyophilized powder. By following these manufacturing protocols, the following siRNA were synthesized (Table 2).

TABLE 2 siRNA synthesized and their end modifications for NuMA.

| RINA | Duplex sequence with overhangs | Yield | SEQ ID NOS |
|---|---|---|---|
| 1 SENSE | 5' r(GAG GUA CGA UUC CGG AGA A)dTdT 3' | 296 µgmL$^{-1}$ | 4 and 5 |
| ANTISENSE | 5' r(UUC UCC GGA AUC GUA CCU C)dTdT 3' | | |
| 9 SENSE | 5' r(GAC CAU GAG GAC GGG CUA AAC)dTdT 3' | 325 µgmL$^-$ | 6 and 7 |
| ANTISENSE | 5' r(GUU UAG CCC GUC CUC AUG GUC)dTdT 3' | | |
| 25 SENSE | 5' r(CGA GAA GGA UGC ACA GAU AGC CA)dTdG 3' | 297 µgmL$^{-1}$ | 8 and 9 |
| ANTISENSE | 5' r(CAU GGC UAU CUG UGC AUC CUU CUC GGU)3' | | |
| 10 SENSE | 5' r(GAG GAG GAA GCG CCC AAU AUC)dTdT 3' | 325 µgmL$^{-1}$ | 10 and 11 |
| ANTISENSE | 5' r(GAU AUU GGG CGC UUC CUC CUC)dTdT 3' | | |

1. 2'-t-butyldimethylsilyl (TBDMS)
2. 2'-O-triisopropylsilyloxymethyl (TOM)
3. 2'-acetoxyethoxy chemistry (ACE)

The cycle began with the 3'-most nucleoside attached to a solid support material or bead. The second nucleotide was coupled to the 5-hydroxyl of the first nucleoside. Capping prevented the propagation of failed or short nucleosides. The internucleotidic phosphate bond was then oxidized to the final P (V) state. Finally, the 5'-protecting group on the new nucleotide was removed and the growing oligonucleotide is ready for addition of the next nucleotide. Once a nucleic acid RINA 10 is a scrambled sequence, meaning that it does not target any gene of interest. This was used as a negative control and referred to in experiments as mock treated.

Example 3
Expression Analysis of NuMA in Different Cancer Cell Lines

A) Gene Expression Analysis by Quantitative Real Time PCR:

The Levels of NuMA were compared in different cancer cell-lines against those of normal diploid cells (retinoid pigmented epithelial cells (RPE-19) and human fibroblasts (HFF-2)). The expression levels of genes was compared by quantitative real time PCR. The cancer cell lines used in this study include breast cancer cell lines (HTB-26, MCF-7 & SKBR-3), colorectal cancer cells (CCL-247 & HTB-38), non small cell lung cancer cell line (A549) and cervical cancer cell lines (HeLa). The preparation of first strand cDNA for real time PCR analysis was carried out using Qiagen Fast lane cell cDNA kit with minor modifications. Briefly 20,000 cells were pelleted and washed once with buffer FCW (Qiagen, Germany) Cells were lysed for 15 min at room temperature using buffer FCP (Qiagen, Germany). Genomic DNA contamination was eliminated by the addition of gDNA wipeout buffer (Qiagen, Germany) by incubating at 42.5° C. for 30 min. First strand cDNA was synthesized by the addition of Quantiscript reverse transcriptase at 42.5° C. for 45 min followed by incubation at 95° C. for 3 min. The first strand cDNA prepared was either used immediately for quantitative real time PCR, or stored till further use at −20° C.

Cell lines were maintained at a confluence of 60-70%. Fresh medium was added 24 h prior to harvest. The first strand cDNA was prepared as described above from the experimental cells following the protocol of the Fast lane cell cDNA kit (Qiagen).

The expression of NuMA in cancer cells varied by several fold in comparison with that of the normal diploid cells. Of the cancer cell lines tested, breast cancer cell lines SKBR-3 showed the highest expression (365% & 308% respectively of HFF-2 & ARPE-19 cells) while, in case of cervical cancer cell lines, Hela, NuMA was under expressed (61.61% and 51.95% respectively of normal cell lines, HFF-2 & ARPE-19), as shown in Table 3.

TABLE 3

Percent change in expression levels of NuMA in different cancer cell lines compared with that of non-cancerous cell lines

| | % Expression | |
|---|---|---|
| Cell Line | HFF-2 (100% Expression) | ARPE-19 (100% expression) |
| HTB-26 | 108.4 | 91.49 |
| CCL-247 | 195.9 | 165.17 |
| MCF-7 | 120.2 | 101.39 |
| SKBR-3 | 365.5 | 308.20 |
| HCC-38 | 77.06 | 64.94 |
| A549 | 66.8 | 56.34 |
| HeLa | 61.61 | 51.95 |
| HTB-38 | 153.04 | 129.1 |

Example 4

Testing of Efficacy

A) In Different Cell Lines:
Oligonucleotide Transfections/siRNA Transfections:

HTB-26, MCF-7, HCC-38 and SKBR-3 (Breast cancer cells), CCL-247 and HTB-38 (colorectal cancer), A549 (lung cancer), HeLa (cervical cancer), PC-3 (Prostate cancer), A431 (Epidermoid cancer), HFF-2 (normal diploid fibroblasts) and ARPE-19 (normal diploid retinal pigmented epithelial cells) cell lines were obtained from ATCC and were maintained at 70-80% confluence with a change of medium prior to 24 h of transfection in T-25 flasks. Cell lines used for transfections of siRNA did not exceed passage number ten. At the time of transfection, cells were trypsinized and reseeded into either a 24-well plate or any other standard tissue culture disposable plastic ware at the appropriate cell density. Unless otherwise stated, all transfections were carried-out in a 24-well plate with varying cell densities depending on the cell lines used for a given experiment. Each well of a 24-well plate was seeded with appropriate cell densities one hour prior to transfection, with growth medium not exceeding 40 µL, and incubated at 37° C. incubator in 5% CO2. Diluted siRNA was made to a final concentration of 10 nM (in 97 µL of Opti-MEM I added 0.3 µL of siRNA from a 20 µM stock), to which was added 3 µL of Hiperfect transfection agent (Qiagen), with vortexing and incubating at room temperature for 10 min. In all experiments a negative control of RINA 10 was used.

The siRNA-liposome complexes were mixed thoroughly and added drop wise gently to each well containing cells, mixed, then incubated at 37° C. in 5% $CO_2$. Transfection efficiencies were obtained for each cell line by counting number of cells showing Cy3 labeled siRNA 16 h after transfection. Cells were trypsinised, washed once in PBS, and suspended in PBS. Cells were observed with an inverted fluorescent microscope and the number of fluorescent cells and total number of cells were counted from 15 different fields. The percentage of Cy3 labeled cells corresponds to the transfection efficiency, and ranged from 70% in case of lung cancer cell line A549, to 99% for breast cancer cell line MCF-7.

TABLE 4

Percent of Transfection efficiencies as determined by Cy3 labeled siRNA for different cell lines.

| Cell line transfected | % of Transfection |
|---|---|
| HTB-26 | 98.00 ± 0.9 |
| MCF-7 | 99.00 ± 0.2 |
| HCC-38 | 90.00 ± 4.0 |
| SKBR-3 | 96.00 ± 0.5 |
| CCL-247 | 96.00 ± 1.6 |
| A549 | 70.00 ± 1.0 |
| HeLa | 97.00 ± 5.0 |
| PC3 | 85 ± 3.0 |
| HFF-2 | 93 ± 1.0 |
| ARPE-19 | 85 ± 5.0 |

B) Knockdown of NuMA in Colorectal Cancer Cell Line, CCL-247 Fails to Localize to Spindle Poles:

The effect of NuMA knockdown on cell morphology and its distribution was studied by the transfection of colorectal cells CCL-247 with RINA 25 and RINA 10. At the end of 72 h of transfection, the cells were fixed for 5 min in ethanol followed by immunoflourescent staining following the protocol of Goding J W., "Monoclonal Antibodies: principles and practice," $3^{rd}$ ed. London: Academic Press. p 141-191; 352-399 (1996). The cells were observed under a fluorescent microscope and untreated cells were compared with cells treated with RINA 25 or RINA 10. NuMA knockdown had no effected on cell morphology. RINA 25 treated cells failed to stain due to reduced levels of NuMA protein either in the cytoplasm or at the spindle poles. In RINA 10 treated or untreated cells, NuMA was observed to localize at the spindle poles during mitosis, and otherwise throughout the cytoplasm, as shown in FIG. 1. The results obtained indicate that RINA 25 successfully knocked down NuMA expression.

C) Identification of Potencies of Different siRNAs Designed in Inhibiting Proliferation of Cancer Cell Lines:

SKBR-3 and HCC-38 (breast cancer) cell lines were transfected with RINA 1, 9, 25 or 10. Twenty four hours after transfection, cells were plated in triplicate at a density of 8000 cells per well, in a 96-well plate. After 72 h, cells were incubated for three hours with BrdU. BrdU incorporation was stopped by the addition of a fixation reagent and cells were permeabilized to allow labeling with anti-BrdU antibody. The antibody is conjugated with horseradish peroxidase (HRP), which converts $H_2O_2$ to a chromogenic product which can be measured by absorbance at 450 nm, with a reference filter at 540 nm. The absorbance led to an estimate of the proportion of cells that were S-phase after treatment with siRNA compared with cells treated with RINA 10 which is a negative control siRNA. All experiments were performed in triplicate and their mean averages and standard deviations were obtained. The statistical significance was determined between RINA 10 treated cells vs RINA 25 treated cells by a paired two tail t-test where $P \leq 0.05$. BrdU incorporation following transfection with RINA 25 was at 69 and 41% respectively for the cancer cell lines SKBR-3 and HCC-38. Treatment of cells with RINA 1 or RINA 9 also lead to decreased BrdU incorporation in compared to RINA 10 treated cells, but less so than RINA 25 treated cells (Table 5). Statistical significance was found between RINA 10 treated and all siRNA treated cells, between RINA 1 and 25, between RINA 9 and 25, between RINA 1 and 9 as well as between RINA 25 and 10. These results indicate that RINA 25 is more potent than RINA 1 and RINA 9.

TABLE 5

*Percent of cells in S-phase of cell cycle as determined by BrdU incorporation after 72 h of siRNA transfection

| Cell line (Cancer) | RINA 1 | RINA 9 | RINA 25 |
|---|---|---|---|
| SKBR-3 (Breast cancer) | 99 ± 0.1 | 91 ± 0.2 | 69 ± 0.19 |
| HCC-38 (Breast cancer) | 51 ± 0.09 | 69 ± 0.01 | 41 ± 0.17 |

*Percentages were derived with respective to RINA 10, negative siRNA treated cells.

D) Real Time Quantitative PCR Analysis:

Without being bound by theory, it is believed that transfection of cells with siRNA results in activation of the RNAi pathway, in which mRNA complementary to the siRNA is degraded, thereby reducing levels of mRNA. The potency of an siRNA may be determined by measuring mRNA levels after siRNA transfection (although a final determination of efficacy should be confirmed by protein levels). Quantitative real time PCR was used to determine the mRNA levels of NuMA among different cell lines transfected with siRNA, compared with untreated cells.

TABLE 6

Fold decrease in mRNA levels of NuMA over untreated controls after 72 h of siRNA transfection for different cell lines

| Cell line | RINA 1 | RINA 9 | RINA 25 |
|---|---|---|---|
| Non-small cell lung cancer (A549) | 4.31 | 2.86 | 4.35 |
| Breast cancer Cell line (MCF-7) | 2.36 | 1.02 | 13.17 |
| Breast cancer cell line (SKBR-3) | 18.18 | 1.66 | 5.04 |
| Epidermoid cancer cell line (A431) | N.D | 3.83 | 3.23 |
| Normal diploid fibroblasts (HHF-2) | 1.24 | 1.21 | 1.06 |

In general, the breast cancer cell lines MCF-7 and HTB-26 showed maximum knockdown efficacy when transfected with RINA 25.

E) Analysis of NuMA Protein Level:

A549, HFF-2, A431 and PC3 cells transfected with siRNA were subjected to total protein extraction after 72 h of transfection. siRNA treatment reduced NuMA protein levels expression by as much as 90% (e.g. FIG. 2) compared to negative siRNA treated samples. The decline in protein expression reflects the decline in mRNA levels seen with real time PCR.

Figure 2A:
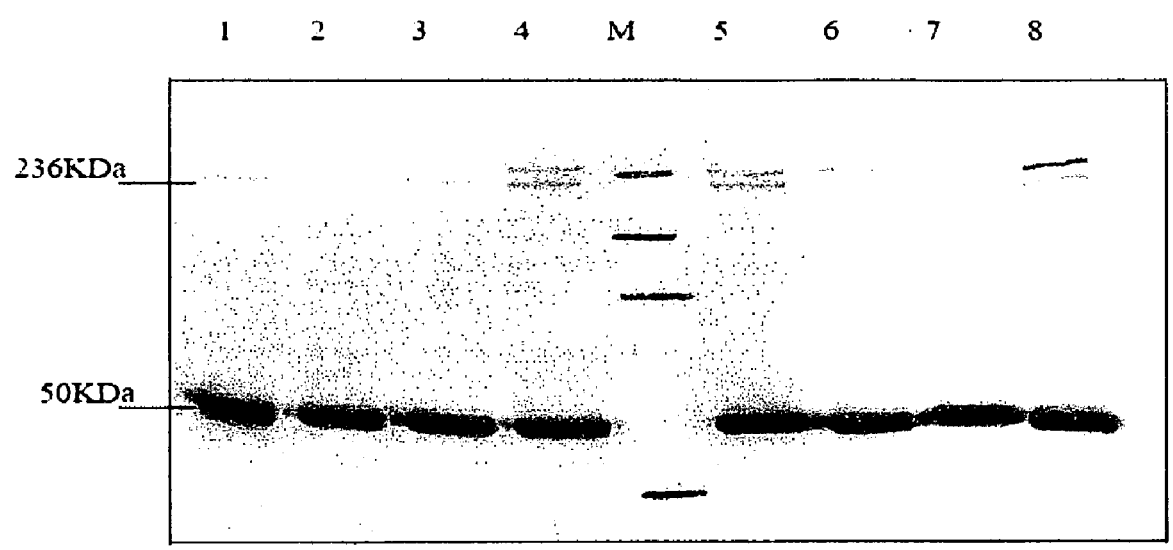
FIG. 2A: Western blot showing knock down of NuMA protein after 72 h of siRNA transfection where 236 KDa represents NuMA protein. Endogenous control tubulin was represented by 50 KDa protein band. Lane M represents molecular weight markers. Lanes 1-4 represents lung cancer cell line A549 transfected with RINA 1, 9, 25 & 10 respectively. A very faint band of NuMA is present in all siRNA transfected cells in comparison over mock treated cells. Lanes 5-8 represents normal fibroblasts cell line MCF-7 transfected with RINA 1, 9, 25 & 10. A very faint band of NuMA is present in all siRNA transfected cells in comparison over mock treated cells.
Figure 2B:
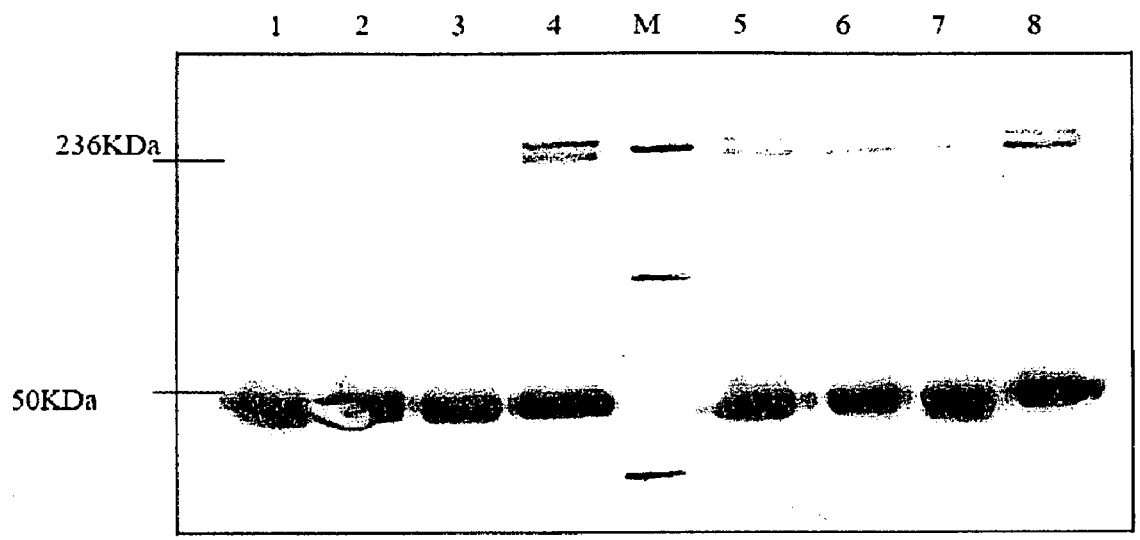
FIG. 2B: Western blot showing knock down of NuMA protein after 72 h of siRNA transfection where 236 KDa represents NuMA protein. Endogenous control tubulin was represented by 50 KDa protein band. Lane M represents molecular weight markers. Lanes 1-4 represents epidermoid cancer cell line A431 transfected with RINA 1, 9, 25 & 10. A very faint band of NuMA is present in all siRNA transfected cells in comparison over mock treated cells. Lanes 5 & 4 represents prostate cancer cell line PC3 transfected with RINA 1, 9, 25 & 10. A very faint band of NuMA is present in all siRNA transfected cells in comparison over mock treated cells.
Figure 2C:
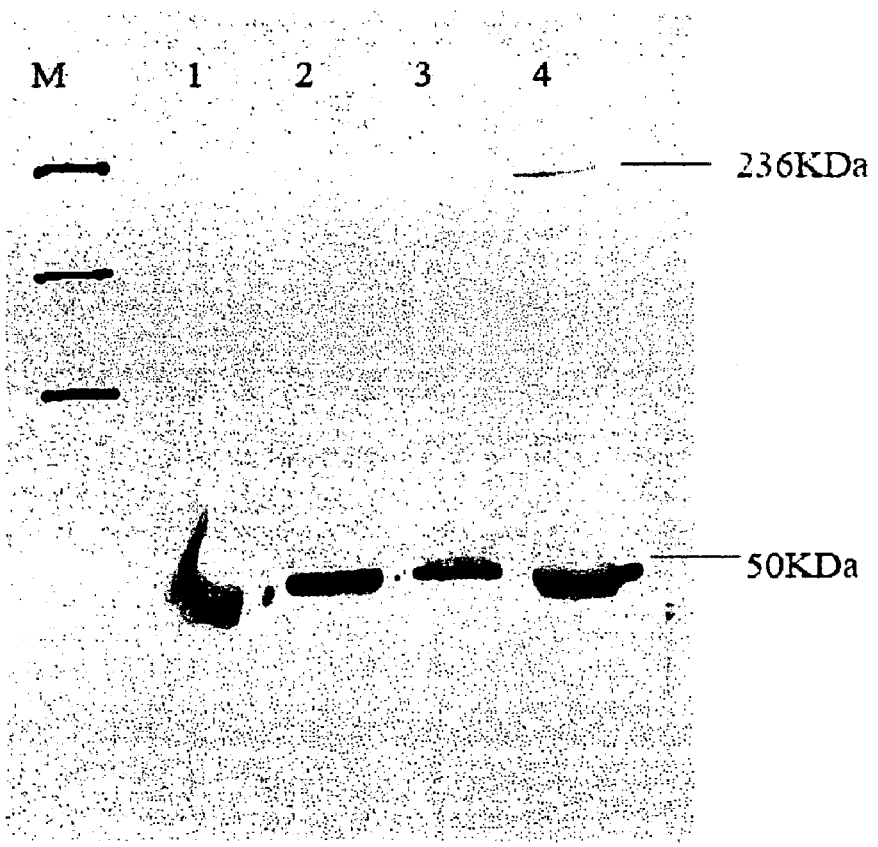
FIG. 2C: Western blot showing knock down of NuMA protein after 72 h of siRNA transfection where 236 KDa represents NuMA protein. Endogenous control of tubulin was represented by a 50 KDa protein band. Lane M represents molecular weight markers. Lanes 1-4 represents cervical cancer cell line HeLa transfected with RINA 1, 9, 25 & 10. A very faint band of NuMA is present in all siRNA transfected cells in comparison over mock treated cells.

Of the different RINA, RINA 25 completely knocked down the protein levels as we observed in FIG. 2, compared with that of RINA 1 and 9, where traces of protein were observed.

Example 5

In-Vitro Testing for Anti Cancer Properties

Figure 3:
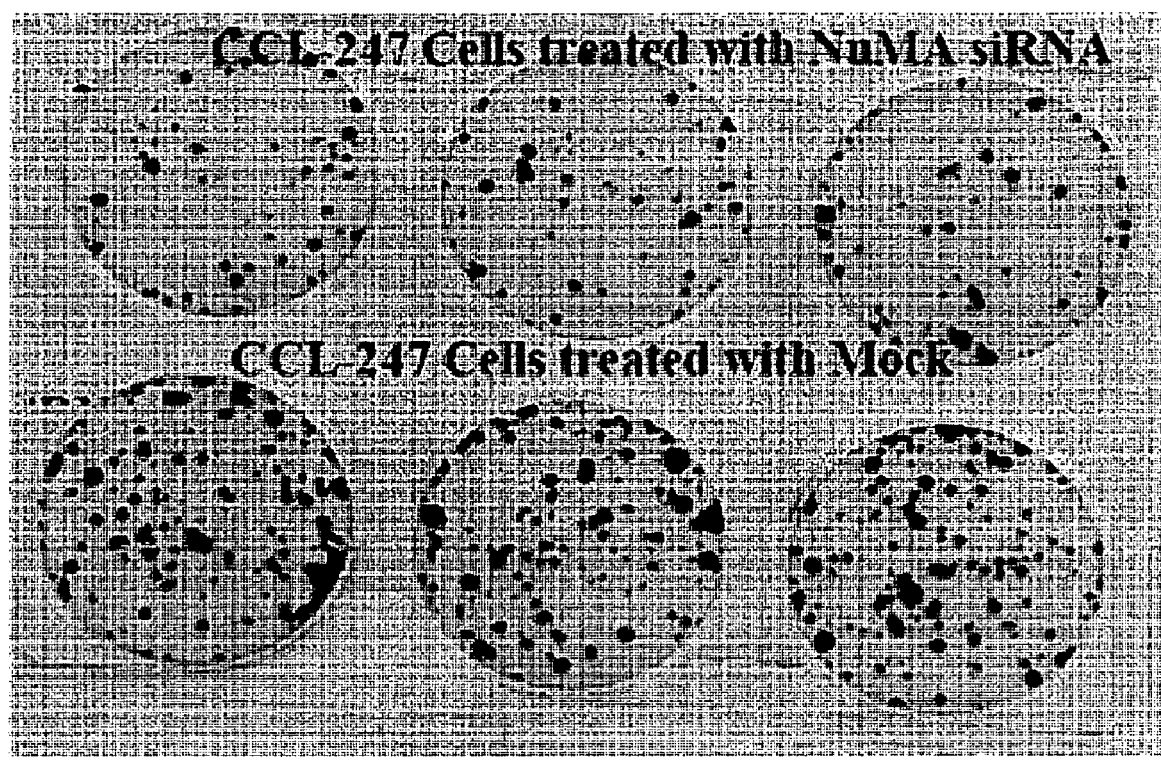
FIG. 3: Colony forming efficiency of siRNA tested by seeding 300 cells per well of a 6-well plate in triplicate each. At the end of 10 days of incubation the number of colonies was counted after crystal violet staining. The mean average percent of number of colonies has been determined with respective to negative siRNA treated controls.

A) Colony Forming Assay:

Colony forming assays were used to assess the ability of siRNA-treated cells to initiate and develop a tumor. 24 h after transfection of cells (Hela, A549 & CCL-247) in 24-well plates, the cells were trypsinized, counted, and replated at a concentration of 300 cells per 6-well plate, in triplicate. Controls of mock treated and untreated cell lines were also prepared. After 10 days of incubation, cells were washed once with PBS and stained with 300 µL of 0.1% crystal violet for 5 min. before washing three times with PBS. This can be seen readily in FIG. 3 which shows CCL-247 cancer cells.

Colonies having at least 60 cells were counted under a light microscope. The percentage of colony formation inhibition was obtained using the following formula:

Rate of colony formation inhibition=(Control colony forming rate−experimental colony forming rate)/ control colony forming rate×100.

The mean percent and standard deviation of colony forming units was derived from average of triplicates for each treatment. The percentage of colony forming efficiency/survivability was obtained with respective to the mock treated cells.

TABLE 7

Percent of colony forming units (CFU) as determined by crystal violet staining after 10 days of siRNA transfection over mock treated controls.

| Cell line | Treatment | % of colony formation |
|---|---|---|
| Hela (Cervical cancer) | RINA 25 | 56.00 ± 2.15* |
| | RINA 10 | 99.50 ± 6.95 |
| | Untreated | 100.00 ± 0.2 |
| A549 (Non small cell lung cancer) | RINA 25 | 78.60 ± 2.47* |
| | RINA 10 | 105.18 ± 9.73 |
| | Untreated | 100.01 ± 0.11 |
| CCL-247 (Colorectal Cancer | RINA 25 | 58.65 ± 27.26* |
| | RINA 10 | 90.00 ± 0.38 |
| | Untreated | 100.00 ± 6.0 |

*Statistically significant over untreated and mock treated cells where $P \leq 0.05$.

The treatment of different cell lines inhibited colony forming ability from 56 to 78% over untreated cells, depending on the cell line (Table 7). HeLa cells showed minimum colony formation (56%) where as A549 cells showed maximum colony formation (78%).

B) Effect of siRNA Transfection on Cancer Cytotoxicity and/ or Membrane Integrity:

LDH release was used to determine the cytotoxicity of reduced levels of NuMA on transfected cells. Cancer cell lines were transfected with siRNA and plated at a density of 20,000 cells/well in a 24-well plate, in triplicate. After 72 h, cells were briefly centrifuged to clear dead floating cells, and 100 µL of spent medium was withdrawn into a separate 96-well plate to assess LDH, following the protocol of Sigma LDH assay kit, TOX-7. The absorbance values were measured at 490 nm with a reference filter of 690 nm. The mean and standard deviation was calculated from triplicate wells and compared against untreated cells as shown in Table 8.

The results obtained indicated that there was no significant release of LDH from any of the cell lines tested in comparison with that of RINA 10 treated cells. This indicates that the inhibition of NuMA expression is not cytotoxic.

TABLE 8

Effect of knock down of NuMA in various cancer cell lines on release of LDH*

| Cell line | Treatment | % LDH release |
|---|---|---|
| HTB-26 | RINA 25 | 114.39 ± 5.30 |
| | RINA 10 | 103.58 ± 3.68 |
| | Untreated | 100.00 ± 0.01 |
| CCL-247 | RINA 25 | 173.82 ± 22.23 |
| | RINA 10 | 210.39 ± 35.58 |
| | Untreated | 100.00 ± 0.005 |
| MCF-7 | RINA 25 | 315.50 ± 4.853 |
| | RINA 10 | 233.12 ± 9.238 |
| | Untreated | 100.00 ± 0.0022 |
| SKBR-3 | RINA 25 | 131.24 ± 36.86 |
| | RINA 10 | 124.49 ± 16.02 |
| | Untreated | 100.00 ± 0.003 |
| HCC-38 | RINA 25 | 133.60 ± 11.28 |
| | RINA 10 | 119.52 ± 3.73 |
| | Untreated | 100.00 ± 0.004 |
| PC3 | RINA 25 | 105.62 ± 1.16 |
| | RINA 10 | 98.30 ± 0.48 |
| | Untreated | 100.00 ± 0 |
| Hela | RINA 25 | 267.58 ± 64.45 |
| | RINA 10 | 240.99 ± 75.11 |
| | Untreated | 100.00 ± 0.005 |
| A549 | RINA 25 | 141.17 ± 26.66 |
| | RINA 10 | 112.05 ± 5.95 |
| | Untreated | 100.00 ± 0 |

*No Statistical significance was found over negative control RINA 10 treatment.

C) Effect of siRNA Transfection on Cell Cycle of Cancer Cell-Lines:

Because cancer cells always remain in a state of proliferation, the number of cells remaining at a given time in the S-Phase of cell cycle determines the growth potential of a tumor. siRNA transfected cells (breast cancer cells HTB-26, MCF-7, HCC-38, colorectal cancer cells CCL-247, lung cancer cells A549, cervical cancer cells HeLa and prostate cancer cells PC3) were plated at a density of 8000 cells per well in a 96-well plate to determine the effect of RINA 25 on cell cycle and, thus, their ability to control the growth index of tumor cell-lines. 72 h after transfection, cells were subjected to BrdU incorporation to determine the number of cells that were in the S-phase of cell cycle as described above. From the absorbance values the percent of cells that were in S-phase of the cell cycle was obtained with reference to the mock treated cells. All experiments were performed in triplicate and their mean averages and standard deviations were obtained.

TABLE 9

Percent of cells that were S-phase of cell cycle as determined by BrdU incorporation after 72 h of siRNA transfection.

| Cell line (Cancer) | RINA 25 | RINA 10 |
|---|---|---|
| HTB-26 (Breast) | 68.90 ± 6.12* | 99.56 ± 5.68 |
| MCF-7 (Breast) | 75.85 ± 3.45* | 92.90 ± 8.22 |
| HCC-38 (Breast) | 41.00 ± 0.17* | 99.44 ± 25.03 |
| SKBR-3 (Breast) | 69.19 ± 0.19* | 99.78 ± 1.95 |
| CCL-247 (colorectal) | 53.53 ± 53.04* | 84.11 ± 38.72 |
| A549 (Lung) | 82.47 ± 16.53 | 90.09 ± 7.71 |

TABLE 9-continued

Percent of cells that were S-phase of cell cycle as determined by BrdU incorporation after 72 h of siRNA transfection.

| Cell line (Cancer) | RINA 25 | RINA 10 |
|---|---|---|
| HeLa (Cervical) | 85.33 ± 0.93* | 96.64 ± 17.55 |
| PC3 (Prostate) | 78.79 ± 5.73* | 100.34 ± 1.95 |

*Statistically significant over untreated where P ≦ 0.05 as determined by student's t-test.

Of the cell lines tested, breast cancer cell line HCC-38 showed only 41% cells in S-phase of cell cycle whereas cervical cancer cells Hela showed 85% in S-phase, over mock treated cells.

D) Effect of NuMA Knockdown on Cell Cycle:

Cancer cell lines transfected with RINA 25 and RINA 10 were harvested after 72 h. The cells were washed with PBS and fixed in 70% ice-cold ethanol at 4° C. for 60 min. Cells were then washed with PBS and treated with propidium iodide for 30 min at 4 C. Propidium iodide stained cells were subjected to flow analysis using FACS caliber, Becton Dickinson. Data were acquired for 10,000 gated events using Cell quest software and analyzed using ModfitLT2.0 (Verity Software House, Topsham, Me.). NuMA knock down results in induction of apoptosis.

Figure 4A:
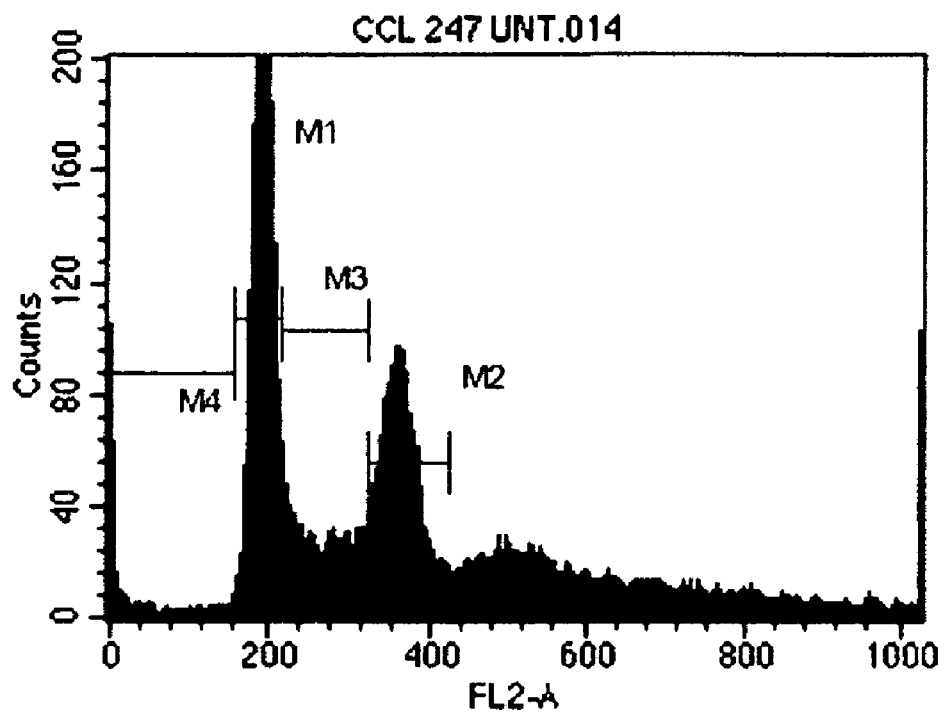
FIG. 4A: Untreated colorectal cancer cells CCL-247 after 72 h of culture were analyzed for cell cycle.
Figure 4B:
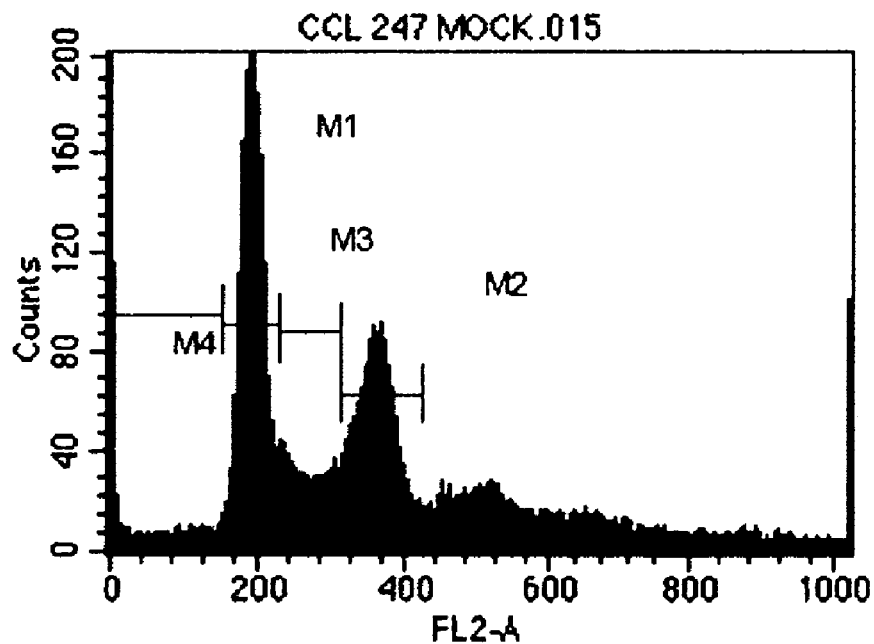
FIG. 4B: RINA 10 treated colorectal cancer cells CCL-247 after 72 h of culture were analyzed for cell cycle.
Figure 4C:
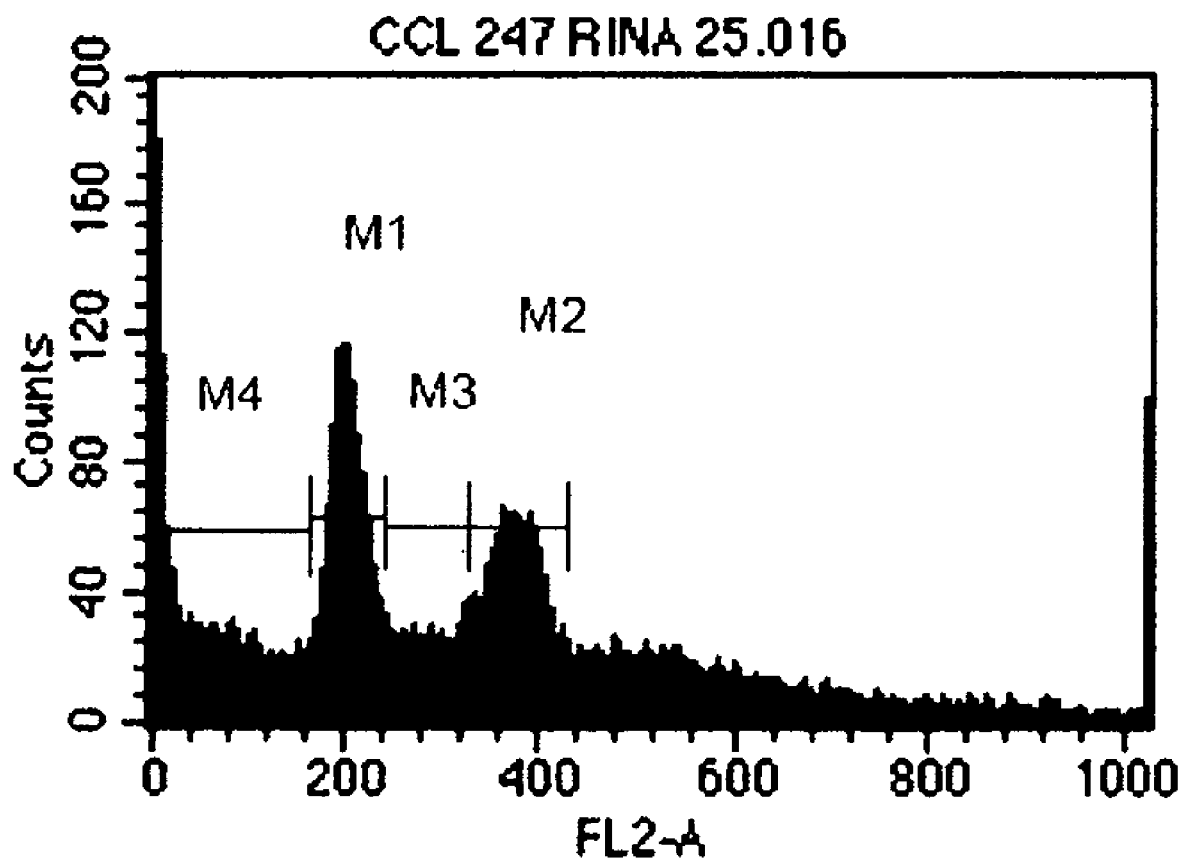
FIG. 4C: RINA 25 treated colorectal cancer cells CCL-247 after 72 h of culture were analyzed for cell cycle.

Knock down of NuMA (using RINA 25) resulted in induction of apoptosis in non small cell lung cancer cells A549, in breast cancer cells MCF-7 and colorectal cancer cell lines CCL-247, as shown in Table 11 and 12, as well as in FIG. 4. Further NuMA knockdown also inhibited the S-phase of the cell cycle which is indicative of proliferation potential of cancerous cells.

TABLE 10

Inhibition of NuMA in cancer Flowcytometry analysis of cancer cell lines transfected with RINA 25 for 72 hrs.

| Cell line and Apoptosis | Phase of cell cycle at 72 hrs. | RINA 25 knocked down cells in % | RINA 10 treated cells in % | Untreated |
|---|---|---|---|---|
| A549 | Go/G$_1$ | 44.95 | 67.12 | 70.59 |
| | S | 05.36 | 10.10 | 09.14 |
| | G$_2$/M | 04.98 | 07.80 | 09.21 |
| | Apoptosis | 43.53 | 13.68 | 09.90 |
| MCF-7 | Go/G$_1$ | 18.73 | 22.34 | 44.16 |
| | S | 02.88 | 14.97 | 21.66 |
| | G$_2$/M | 07.97 | 12.88 | 03.82 |
| | Apoptosis | 66.02 | 42.39 | 14.29 |
| CCL-247 | Go/G$_1$ | 21.83 | 33.16 | 34.41 |
| | S | 08.95 | 11.07 | 23.09 |
| | G$_2$/M | 20.16 | 23.79 | 12.75 |
| | Apoptosis | 27.08 | 06.46 | 02.53 |

E) Induction of Interferon Response by siRNA Transfection of Various Cancer Cell Lines:

RINA 25 and 10 were transfected into different cancer cell lines as described elsewhere and incubated for 72 h in 24-well plates. At the end of 72 h, plates were centrifuged to remove dead cells, and 100 μL of supernatants were incubated at 4° C. in round bottom ELISA plates. Wells were then washed with PBST (phosphate buffered saline containing 0.1% Tween 20) to remove unbound antigen, incubated with 5% skim milk powder for 30 min at room temperature. Wells were then washed, as before, three times with PBST, and incubated with HRP-conjugated goat anti-rabbit antibodies for additional 1 h at room temperature. At the end of the incubation time, HRP substrate was added. Absorbance values were measured from triplicates and results are shown in Table 11 and 12.

TABLE 11

Effect of siRNA transfection on induction of interferon α response

| Cell line | siRNA | Interferon α response (ng) |
|---|---|---|
| HTB-26 | RINA 25 | 19.03 ± 17.9222* |
|  | RINA 10 | 18.27 ± 17.7443 |
|  | Untreated | 18.30 ± 18.3225 |
|  | BSA | 17.11 ± 18.0524 |

*Indicates statistically no significance over other treatments at $P \leq 0.05$ as determined by student's t-test.

TABLE 12

Effect of siRNA transfection on induction of interferon β response

| Cell line | siRNA | Interferon β response (pg/ml) |
|---|---|---|
| HTB-26 | RINA 25 | 2.82 ± 0.5720* |
|  | RINA 10 | 2.69 ± 0.4480 |
|  | Untreated | 2.66 ± 0.2619 |
|  | BSA | 2.48 ± 0 |

*Indicates statistically not significant over other treatments at $P \leq 0.05$ as determined by student's t-test.

siRNA transfection is often associated with IFN α and IFN β production. However, there was no statistically significant release of neither IFN alpha or IFN beta in both RINA treated and untreated cells, indicating that RINA 25 did not elicit any IFN α response.

F) Effect on Transcription:

To test the specificity of siRNA, breast cancer cells HTB-26 were transfected by siRNA, as described above. At the end of 72 h of transfection, total RNA was prepared following the protocol of Qiagen total RNA isolation kit (RNeasy Mini kit). Total RNA of 2 μg was suspended in 104 of water. The quality of RNA was checked on a Bioanalyzer using a nano-chip from Agilent technologies. One μg of total RNA was converted into biotinylated, amplified RNA for hybridization with Illumina Sentrix arrays. The steps involved during this procedure include reverse transcription using Array Script of total RNA with oligo (dT) primer bearing a T7 promoter. Second strand synthesis was achieved using DNA polymerase and RNase. The double strand cDNA was purified, and was subject to in vitro transcription to synthesize biotinylated cRNA. cRNA was hybridized (8-sample chip of Human whole genome) overnight, and probed with streptavidin-Cy3. At the end of detection Illumina Bead chips were dried and scanned with Bead Studio analyzer software. The results obtained were analyzed for differential expression of genes between untreated, RINA 10 treated and RINA 25 treated samples.

Figure 5:
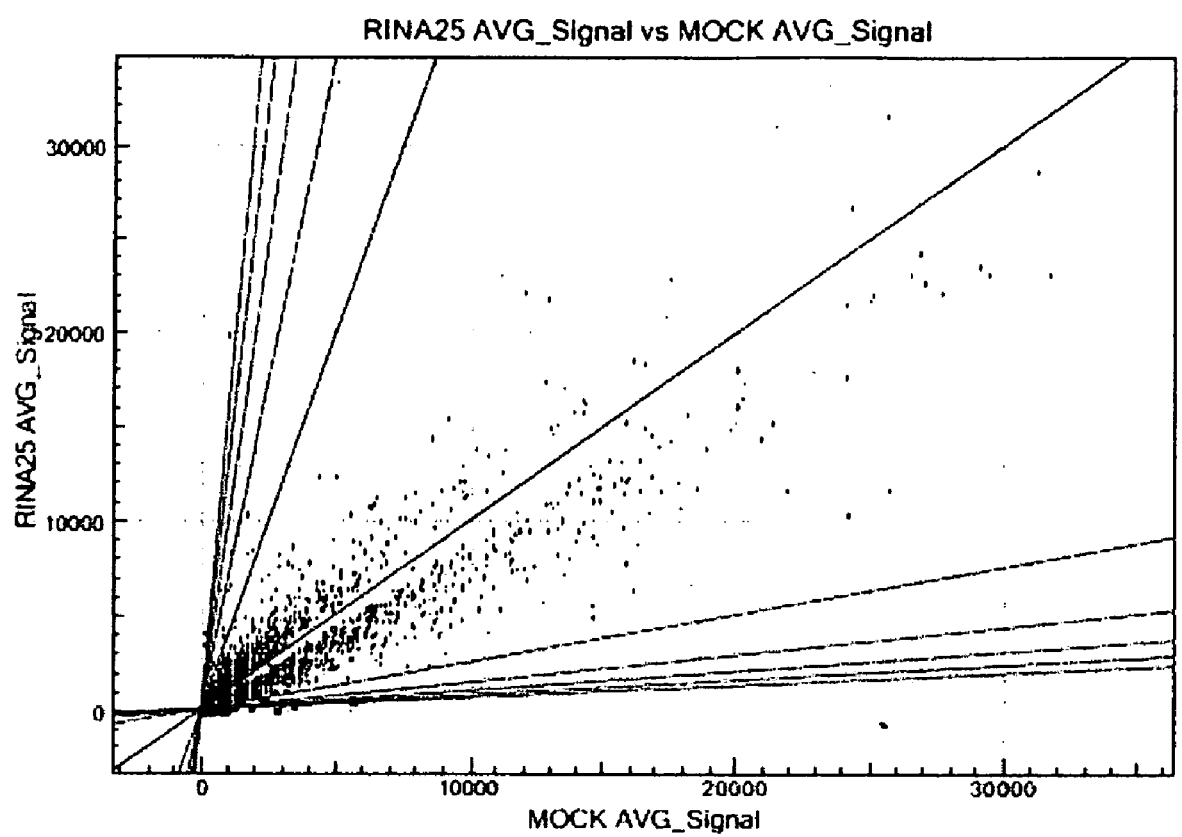
FIG. 5: Effect of repression of NuMA by RINA 25 in HTB 26 breast cancer cells, by microarray analysis. Microarray analysis identified a total of 350 genes upregulated while 300 genes were down regulated in comparison with that of the RINA 10 treated cells.

Using Bead studio analyzer differential expression software, average signals were normalized and performed a "t test" at a differential ("diff") score of +/−13.6. All the differentially expressed genes between RINA 25, RINA 10, and untreated samples were identified. The probe IDs that were differentially expressed were sorted for the number of genes either down regulated or unregulated. The change in transcriptome expression levels is indicated in FIG. 5, showing a number of genes that are either upregulated or down regulated with respect to the negative siRNA treated controls.

G) Efficacy Studies in Nude Mice

Figure 6:
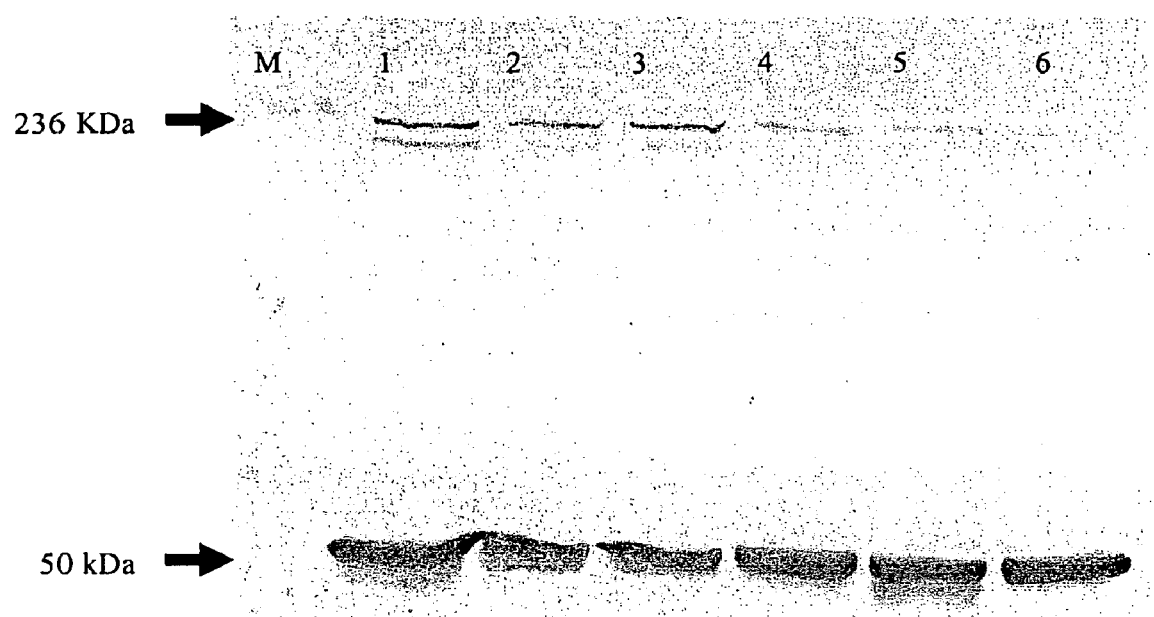
FIG. 6: Western blot of tumors. Lane 1 represents molecular weight marker. Lanes 2,3 & 4 represent placebo treated animals A-1, A4 and A-10 respectively. Lanes 5,6 & 7 represent RINA 25 treated animals B-2, B-9 & B-11 respectively. Arrowhead indicates 236 KDa NuMA and 50 KDa tubulin. The NuMA band in lanes 4,5 & 6 were faint in nature when compared corresponding bands in lanes 2,3 & 4. This indicates that the animals treated with RINA 25 showed decreased levels of protein when compared with that of placebo treated animals.

To test the efficacy of siRNA in vivo, xenograft colorectal cancer tumors were induced in 6-8 week old female Nude mice by subcutaneously injecting, into one flank, human colorectal cancer cell-line CCL247 at a density of 10 million cells in 1004, volume of PBS. Mouse developed tumors of approximately 80-100 mm$^3$ by the end of two weeks. Mouse were divided into two groups. Group B consisted of three animals treated with RINA 25 while Group A consisted of three animals treated with placebo. Animals were treated every alternative day with 10 mg of RINA per kg of body weight. After five doses, the tumors were retrieved and analysed by protein blot for NuMA knockdown. In RINA 25-treated animals there was a decrease in NuMA levels over placebo treated animals (FIG. 6). This indicates that RINA 25 is capable of knocking down NuMA under in vivo conditions in colorectal cancer. Of the three animals, animal B-11 showed least percent growth rate on Day 7 as well as day 11 in comparison with that of all other animals. (Table 13).

TABLE 13

Effect of knockdown of NuMA by RINA 25 on tumor regression

| *Group - Animal no. | % growth rate ||| 
|---|---|---|---|
|  | Day 1 | Day 7 | Day 11 |
| A-1 | 100 | 181.05 | 380.48 |
| A-4 | 100 | 192.58 | 262.16 |
| A-10 | 100 | 323.69 | 498.49 |
| B-2 | 100 | 390.83 | 606.73 |
| B-9 | 100 | 258.18 | 291.58 |
| B-11 | 100 | 171.47 | 212.47 |

*Group A - Indicates Placebo treated animals where animals were given non specific nucleic acid. Group B - Indicates animals given RINA 25.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention.

What is claimed is:

1. An siRNA that targets a sequence of SEQ ID NO:3 in NuMA mRNA of Genbank Accession number NM-006185 (SEQ ID NO: 12), wherein the siRNA consists of SEQ ID NO: 8 and SEQ ID NO: 9.

2. A composition for the treatment of cancer, comprising the siRNA of claim 1 and a pharmaceutically acceptable excipient.

3. The composition of claim 2, wherein said cancer is selected from the group consisting of cervical cancer, epidermoid cancer, oral cancer, glioma, leukemia, brain cancer, esophageal cancer, stomach cancer, bladder cancer, pancreatic cancer, cervical cancer, head and neck cancer, ovarian cancer, melanoma, lymphoma, and multidrug resistant cancer.

4. The composition of claim 2, wherein said cancer is selected from the group consisting of colorectal cancer, breast cancer, lung cancer, and prostrate cancer.

5. A composition comprising a short nucleic acid molecule that modulates NuMA expression, wherein the short nucleic acid molecule consists of siRNA 25 consisting of sense strand SEQ ID NO: 8 and antisense strand SEQ ID NO: 9.

* * * * *

UNITED STATES PATENT AND TRADEMARK OFFICE
CERTIFICATE OF CORRECTION

| | | |
|---|---|---|
| PATENT NO. | : 8,188,264 B2 | Page 1 of 1 |
| APPLICATION NO. | : 12/772079 | |
| DATED | : May 29, 2012 | |
| INVENTOR(S) | : Murali Addepalli et al. | |

It is certified that error appears in the above-identified patent and that said Letters Patent is hereby corrected as shown below:

On the Title Page, under Related U.S. Application Data, in Item (63), delete "Jun. 3, 2005" and insert --Jun. 3, 2008--.

Signed and Sealed this
Eighteenth Day of December, 2012

David J. Kappos
*Director of the United States Patent and Trademark Office*